United States Patent [19]

Flouret et al.

[11] Patent Number: 5,373,089
[45] Date of Patent: Dec. 13, 1994

[54] OXYTOCIN ANTAGONIST

[75] Inventors: George Flouret, Deerfield; Laird Wilson, Lisle, both of Ill.

[73] Assignee: Northwestern University, Evanston, Ill.

[21] Appl. No.: 52,887

[22] Filed: Apr. 26, 1993

Related U.S. Application Data

[63] Continuation-in-part of Ser. No. 433,664, Nov. 8, 1989, abandoned, which is a continuation-in-part of Ser. No. 239,780, Sep. 2, 1988, abandoned.

[51] Int. Cl.$^5$ .............................................. C07K 7/16
[52] U.S. Cl. .................................... 530/315; 530/317; 530/328; 930/260; 930/DIG. 565
[58] Field of Search ...................... 530/315, 317, 328; 930/260, DIG. 565; 514/16, 807

[56] References Cited

U.S. PATENT DOCUMENTS 4,597,901  7/1986  Yim ..................................... 530/328

OTHER PUBLICATIONS

Hruby et al, Journal of the American Society, vol. 93, (1971), pp. 5539–5542.
Manning et al, The Pituitary, eds, C. Beardwell & G. Robinson, Butterworths, England, pp. 265–296, (1981).
Hruby et al (The Peptides), Chap. 4, pp. 77–206, 1987.
Akerlund I et al., "Inhibition of Vasopressin Effects on the Uterus by a Synthetic Analogue," Obstet. and Gynecol., 62:309–312 (1983).
Akerlund II et al., "The Effect on the Human Uterus of Two Newly Developed Competitive Inhibitors of Oxytocin and Vasopressin," Acta Obstet Gynecol. Scad. 64:499–504 (1985).
Albrecht et al., "Placental Steroid Hormone Biosynthesis in Primate Pregnancy," Endocrine Reviews 11:124–150 (1990).
Bidlingmeyer et al., "Rapid Analysis of Amino Acids Using Pre-column Derivatization," J. of Chromat. 336:93–104 (1984).
Bodansky et al., "Synthesis and Some Pharmacological Properties of [8-L-Tryptophan] Oxytocin," J. Med. Chem. 23:1258–1261 (1980).
Chan et al., "Some Pharmacologic Studies on 1-L-Penicillamine-oxytocin and 1-Deaminopenicillamine-oxytocin: Two Potent Oxytocin Inhibitors," Endocrinology 81:1267–1277 (1967).
Du Vigneaud et al., "The Synthesis of an Octapeptide Amide with the Hormonal Activity of Oxytocin," J. Am. Chem. Soc. 75:4879–4880 (1953).
Flouret et al., "Design of Potent Oxytocin Antagonists Featuring D-Tryptophan at Position 2," J. Med. Chem. 34:642–646 (1991).
Gisin, "143. The Preparation of Merrified Resins Through Total Esterification With Cesium Salts," Helevetica Chimica Acta 56:1476–1482 (1973).
Holton, Pamela, "A Modification of the Method of Dale and Laidlaw for Standardization of Posterior Pituitary Extract," Brit. J. Pharmacol.:328–334 (1948).
Hope et al., "A Highly Potent Analogue of Oxytocin, Desamino-oxytocin," J. of Biochem. 237:1563–1566 (1962).
Kaiser et al., "Color Test for Detection of Free Terminal Amino Groups in the Solid Phase Synthesis of Peptides," Anal. Biochem. 34:595–598 (1970).
Law et al., "Synthesis of 2-p-Methoxyphenylalanine oxytocin (O-Methyl-oxytocin) and Some Observations on Its Pharmacological Behavior," J. Am. Chem. Soc. 82:4579–81 (1960).

(List continued on next page.)

Primary Examiner—Robert J. Hill, Jr.
Assistant Examiner—T. D. Wessendorf
Attorney, Agent, or Firm—Tilton, Fallon, Lungmus & Chestnut

[57] ABSTRACT

A compound is disclosed for inhibiting the effects of oxytocin in a female mammal. As an analog of oxytocin the compound is named [(S)PMP$^1$,D-Trp$^2$,Pen$^6$,Arg$^8$] oxytocin. This compound can be administered to pregnant women to arrest premature labor while avoiding unwanted side effects due to antagonism of the antidiuretic hormone, vasopressin.

1 Claim, No Drawings

OTHER PUBLICATIONS

McPherson, Grant, "Analysis of Radioligand Binding Experiments: A Collection of Computer Programs for the IBM PC," *J. of Pharm. Meth.* 14:213–228 (1985).

Manning, Maurice I, "Synthesis by the Merrifield Method of a Protected Nonapeptide Amide with the Amino Acid Sequence of Oxytocin," *J. Amer. Chem. Soc.*, 90:1348–1349 (1968).

Manning II et al., "The Purification of Synthetic Oxytocin and Analogues by Gel Filtration of Sephadex G-15," *J. Chromatog.* 38:396–398 (1968).

Manning III et al., "Synthetic Antagonists of In Vivo Antidiuretic and Vasopressor Responses to Arginine-Vasopressin," *J. Med. Chem.* 24:701–706 (1981).

Manning IV et al., "Potent Antagonists of the Antidiuretic Responses to Arginine-vasopressin Based on Modification of [1-(B-Mercapto-B,B-cyclopentamethylenepropionic Acid), 2-D-phenylalanine,4-valine] arginine-vasopressin at Position 4," *J. Med. Chem.* 26:1607–1613 (1983).

Melin et al., "Inhibitory Effect of O-alkylated Analogues of Oxytocin and Vasopressin on Human and Rat Myometrial Activity," *J. Endocr.* 88:173≧180 (1981).

Merrifield, R. B., "Solid Phase Peptide Synthesis. I. The Synthesis of a Tetrapeptide," *J. Am. Chem. Soc.*, 2149–2154 (1963).

Muson et al., "Ligand: A Versatile Computerized Approach for Characterization of Ligand-Binding Systems," *Anal. Biochem.* 107:220–239 (1980).

Pepe et al., "Regulation of the Primate Fetal Adrenal Cortex," *Endocrine Reviews* 11:151–176 (1990).

Porath et al., "Gel Filtration: A Method For Desalting and Group Separation," *Nature* 183:1657–1659 (1959).

Sakakibara et al., "A New Method for Releasing Oxytocin from Fully-Protected Nona-peptides Using Anhydrous Hydrogen Fluoride," *Bull. Chem. Soc. Jpn.* 38:1412–1413 (1965).

Sawyer, Wilbur I, "Differences in the Antidiuretic Responses of Rats to the Intravenous Administration of Lysine and Arginine Vasopressins," *Endocrinology* 63:694–8 (1988).

Sawyer II et al., "The Design of Effective In Vivo Antagonists of Rat Uterus and Milk Ejection Responses to Oxytocin," *Endocrinology* 106:81–91 (1979).

Schild, H. O., "pA, A New Scale For the Measurement of Drug Antagonism," *Brit. J. Pharm.* 2:189–206 (1947).

Wadsworth et al., "Ethyl Cyclohexylideneacetate" in *Organic Synthesis* (Baumgarten ed.) vol. V., pp. 547–549 (1973).

Wilson I et al., "Inhibition of Spontaneous Uterine Contractions During the Last Trimester in Pregnant Baboons by an Oxytocin Antagonist," *Am. J. of Obstet. and Gyn.* 163:1975–1882 (1990).

Wilson II et al., "Inhibition of Oxytocin-Induced Uterine Contractions by an Oxytocin Antagonist in the Pregnant Baboon," *Amer. J. of Obstet. and Gyn.* 165:456–460 (1991).

Wilson III et al., "Forward Shift in the Initiation of the Nocturnal Estradiol Surger in the Pregnant Baboon: Is this the Genesis of Labor?" *Am. J. of Obstet. and Gyn.* 165:1487–1498 (1991).

Yim et al., "A Facile Synthesis of B-Benzylmercapto)-B,B-cyclopentamethylene-priopionic acid," *Int. J. Peptide Protein Res.* 21:568–570 (1983).

OXYTOCIN ANTAGONIST

RELATED APPLICATION

This application is a continuation-in-part of co-pending application Ser. No. 07/433,664 now abandoned, filed Nov. 8, 1989, which is a continuation-in-part of Ser. No. 07/239,780 filed Sep. 2, 1988.

FIELD OF INVENTION

The present invention relates to a novel compound which is highly active as an oxytocin antagonist and which exhibits slight antagonism for vasopressin.

BACKGROUND OF INVENTION

Preterm labor is the major cause of prenatal morbidity and mortality in the United States. Current methods of inhibiting preterm labor are not always successful and are often associated with significant side effects. Since the uterus is a target organ for oxytocin, and assuming that oxytocin is an important contributing factor to preterm labor, the development of a potent oxytocin antagonist would result in successful inhibition of preterm labor with few associated side effects.

Structurally, oxytocin (OT) and antidiuretic hormone (ADH), also called vasopressin, are similar. Their comparative structures are illustrated below.

$$\begin{array}{cccccccccc}1 & 2 & 3 & 4 & 5 & 6 & 7 & 8 & 9 \\ \text{Cys} & \text{Tyr} & \text{Ile} & \text{Gln} & \text{Asn} & \text{Cys} & \text{Pro} & \text{Leu} & \text{Gly-NH}_2\end{array}$$
$$\text{S}\text{————————}\text{S}$$

OXYTOCIN (OT)

$$\begin{array}{cccccccccc}1 & 2 & 3 & 4 & 5 & 6 & 7 & 8 & 9 \\ \text{Cys} & \text{Tyr} & \text{Phe} & \text{Gln} & \text{Asn} & \text{Cys} & \text{Pro} & \text{Arg} & \text{Gly-NH}_2\end{array}$$
$$\text{S}\text{————————}\text{S}$$

VASOPRESSIN (ADH)

Various investigations in the literature have reported the synthesis of antagonists to ADH for the treatment of hypertension and the synthesis of antagonists to oxytocin. In 1960, Law, H. D. and V. DuVigneaud, *J. Am. Chem. Soc.*, 82:4579, reported the first synthesis of an oxytocin antagonist (2-0-methyltyrosine-OT). In 1967, Chan, Fear and DuVigneaud, *Endocrinology*, 81:1267, reported the synthesis of 1-L-Penicillamine-oxytocin and 1-deaminopenicillamine-oxytocin. This was the first study to show an in vivo inhibitory effect of an oxytocin antagonist on uterine contractions and response to oxytocin in the anesthetized rat.

In 1980, Sawyer, et al., *Endocrinology*, 106:81, reported the synthesis of an oxytocin antagonist that combined the two important features of the antagonist of Law and DuVigneaud and of the antagonist of Chan, et al. The new antagonist was (1-deaminopenicillamine, 2-0-methyltyrosine) oxytocin. The new antagonist had a $pA_2$ of 7.8 as determined by the oxytocic bioassay. The $pA_2$ is the negative logarithm of the molar concentration of the antagonist that reduces the response to the antagonist by ½. It is defined by Schild, *British J. Pharmacology*, 26:189 (1947).

In 1983, Manning, et al., *J. Med. Chem.*, 26:1607-161 reported the synthesis of a number of antagonists to ADH. One of these antagonists proved to have potential anti-oxytocic activity [$\beta,\beta$-pentamethylene-$\beta$-mercaptopropionic acid[1],D-Phe[2],Ile[4]] arginine vasopressin with a $pA_2$ of 8.2, or in other words, 2.5 times more potent than the antagonist reported by Sawyer, et al. in 1980 (see page 1610, Table I, compound no. 1). This oxytocin antagonist can be called [Pmp[1],D-Phe[2], Phe[3], Ile[4], Arg[8]] oxytocin. A related oxytocin antagonist, [Pmp[1], D-Trp[2], Phe[3], Ile[4], Arg[8]] oxytocin was disclosed by Wilson and Flouret, Abstract for Society for the Study of Reproduction Meeting Jul. 14–17, 1986.

In 1981, Melin, et al., *Endocrinology*, 88:173, developed an oxytocin antagonist for inhibiting preterm labor. They synthesized 1-deamino, ethyloxytocin which had a $pA_2$ of 7.2. They also showed that this compound inhibited uterine contractions in rats in vivo and in humans in vitro and in vivo (Akerland, et al., *Obstet. and Gynecol.*, 62:309, 1983). In 1985, Akerland, et al., *Obstet. and Gynecol. Scand.*, 64:499, reported the synthesis of 1deamino[D-Tyr(OEt)[2], Thr[4], Orn[8]] vasopressin with a $pA_2$ of 8.3. They have tested this compound in vitro on human uterine tissue and have shown it to inhibit uterine contractions.

U.S. Pat. No. 4,597,901 discloses the class of vasopressin antagonists in which cysteine-1 is present in both oxytocin and vasopressin and substituted with $\beta,\beta$-cylopentamethylene-$\beta$-mercaptopropionic acid. Other amino acids of vasopressin are substituted. The resulting class of compounds is said to be vasopressin antagonists the biological activity being manifested as water diuresis.

SUMMARY OF INVENTION

The present invention comprises an oxytocin antagonist which is an analog of oxytocin. In the compound of this invention, cysteine-1 of oxytocin is substituted with $\beta,\beta$-(3-thiapentamethylene)-$\beta$-mercaptopropionic acid. In addition, L-tyrosine-2 is substituted with D-tryptophan, and penicillamine is substituted for 1-cysteine in the 6 position and L-arginine is substituted in the 8 position for L-leucine. The resulting compound [(S)Pmp[1], D-*Trp*[2], Pen[6], Arg[8]] oxytocin is believed to be novel and has been found to have remarkable properties. It is highly active as an oxytocin antagonist. At the same time, and although it is structurally similar to vasopressin and vasopressin antagonists described in the literature, the new compound exhibits minimal ADH antagonism. When these two antagonisms are expressed as a ratio, the compound of this invention has a very high anti-oxytocin/anti-ADH activity ratio. This combination of properties is highly advantageous for therapeutic use. Effective anti-oxytocin action can be obtained with minimal anti-ADH side effects. The compound of this invention is therefore adapted for inhibiting contraction of the uterine muscle in response to bodily oxytocin, and can be used to suppress preterm labor.

DESCRIPTION OF THE INVENTION

The oxytocin antagonist of this invention is represented by the formula:

$$\begin{array}{cccccccccc}1 & 2 & 3 & 4 & 5 & 6 & 7 & 8 & 9 \\ \text{(S)Pmp} & \text{D} & \text{Trp} & \text{Ile} & \text{Gln} & \text{Asn} & \text{Pen} & \text{Pro} & \text{Arg} & \text{Gly-NH}_2\end{array}$$
$$\text{S}\text{————————}\text{S}$$

wherein Pmp is $\beta,\beta$-(3-thiapentamethylene)-$\beta$-mercaptopropionic acid, D-Trp is the D form of tryptophan, and Ile, Gln, Asn, Pen (Pen=penicillamine), Pro, Arg, are the L forms of isoleucine, glutamine, asparagine, proline and arginine, respectively.

The remarkable properties of the novel compound of this invention are shown by bioassays, which will now be described.

Oxytocin Bioassay

The protocol used for the oxytocin bioassay procedure is derived from procedures described in a paper by Sawyer, et al., *Endocrinology*, 106:81 (1980), which in turn was based on reports of Munsick, *Brit. J. Pharmacol.*, 3:328 (1960), and Holton, *Brit. J. Pharmacol.*, 3:328 (1948). The assay calculations for the $pA_2$ estimates are described by Schild, *British J. Pharmacology*, 2:189 (1947). The major difference in the present procedure from those reported by others in the field is that the area under the contraction is integrated where most other techniques calculate the amplitude. Integration provides much more consistent and reliable results although the $pA_2$ estimates are approximately an order of magnitude lower than those reported using amplitude of the contraction as the endpoint.

Method

1. Animals—a 1.5 cm piece of uterus from a virgin rat (Holtzman) in natural estrus is used for the assay.
2. Buffer/Assay Bath—The buffer used is Munsicks. This buffer contains 0.5 mM $Mg^{++}$ which reduces the $pA_2$ estimates, but the results are reported to correlate better with in vivo data (Sawyer, et al., 1980). The buffer is gassed continuously with 95% oxygen; 5% carbon dioxide giving a pH of 7.4. The temperature of the assay bath is 37° C. A 10 ml assay bath is used that contains a water jacket for maintaining the temperature and inlet and outlet spikets for adding and removing buffer.
3. Polygraph/transducer—The piece of uterine tissue used for the assay is anchored at one end and connected to a Statham Strain Gauge Force Transducer at the other end which in turn is attached to a Grass Polygraph Model 79 for monitoring the contractions.
4. Assay Protocol. (a) The tissue is equilibrated in the assay bath for one hour with washing with new buffer every fifteen minutes. One gram of tension is kept on the tissue at all times.
   (b) The tissue is stimulated initially with oxytocin at 10 nM to "acclimate" the tissue and with 4 mM KCl to determine the maximum contractile response.
   (c) A cumulative dose response curve is then done with oxytocin and a concentration of oxytocin equivalent to approximately 80% of the maximum is used for estimating the $pA_2$ of the antagonist.
   (d) The tissue is exposed to oxytocin (Calbiochemical, San Diego, Calif.) for one minute and washed out. There is a three minute interval before addition of the next dose of the agonist or antagonist. When the antagonist is tested, it is given five minutes before the agonist. The agonist is given for one minute. All responses are integrated using a 7P10 Grass Integrator. This is the major difference between the present protocol and others in the literature which usually measure amplitude of the contractions as the response. A single concentration of oxytocin, equal to 80% of the maximum response, is used to test the antagonist. Three different concentrations of antagonists are used, two that will reduce the response to the agonist by less than 50% and one that will reduce the response greater than 50% (ideally this relation would be 25%, 50% and 75%). This is repeated three times for each dose of antagonist for a three point assay.
   (e) Calculations for $pA_2$: The dose-response (DR) ratios are calculated for antagonist and a Schild's Plot is performed by plotting the Log (DR-1) vs. Log of antagonist concentration. The line plotted is calculated by least squares regression analysis. The $pA_2$ is the concentration of antagonist at the point where the regression line crosses the 0 point of the Log (DR-1) ordinate. The $pA_2$ is the negative Log of the concentration of antagonist that will reduce the response to the agonist by one-half.

As an analog of oxytocin, the novel compound of this invention may be designated as $[(S)Pmp^1, D\text{-}Trp^2, Pen^6, Arg^8]$ oxytocin. When this compound was tested by the above-described assay for competitive antagonism with oxytocin, in an average of ten assays, the $pA_2$ value was found to be greater than 8.86.

ADH-Bioassay

The above compound was also tested for antagonism to vasopressin. Anti-ADH activity can be determined by measuring the alteration in urine output due to ADH in the presence and absence of the antagonist. A suitable ADH-assay is described in Sawyer, et al., *Endocrinology*, 63:694 (1958). When tested by this method, it was found that the compound $[(S)Pmp^1, D\text{-}Trp^2, Pen^6, Arg^8]$ oxytocin exhibited very low activity as a vasopressin antagonist. The ratio of oxytocin antagonism to ADH antagonism was very high, viz. over 1, 866, as compared with 200 for the compositions disclosed in the parent applications.

By virtue of its oxytocin antagonist activity with minimal vasopressin antagonism, the compound of this invention will be useful in treating symptoms requiring an oxytocin antagonist in humans and animals. It can be used to inhibit uterine contractions and milk letdown as well as to inhibit preterm labor. Although the structure of the compound resembles both oxytocin and vasopressin, it exhibits not only increased anti-oxytocin activity but also greatly decreased anti-ADH activity. This compound might also be useful for inhibiting dysmenorrhea or serving as an antidote for over stimulation of uterine contraction during labor induction with oxytocin or for treating hypertension.

The compound of this invention can be administered to women by various known routes of administration. For hospital use, intravenous infusion will usually be the administration route of choice. However, the compound may also be administered intraperitoneal, subcutaneously, or intramuscularly. Oral administration may also be feasible. If required, tablets or capsules for oral use may be provided with an enteric coating protecting the compound from destruction in the stomach while permitting its release in the intestinal tract. The sublingual administration by providing suitable doses of this compound in tablet triturates placed under the tongue may also be practical. This is the way the hormone oxytocin is given to induce milk let-down from the breasts of the lactating mother.

An effective but nontoxic quantity of the compound is employed in this treatment. The dosage regimen for preventing or treating symptoms by the compound of this invention is selected in accordance with a variety of factors including the type, age, weight, sex and medical condition of the woman, the severity of the symptoms and the route of administration of the compound. An ordinary medical practitioner can determine and prescribe the effective amount based on the route of administration of the oxytocin antagonist to prevent or arrest the progress of the condition to be inhibited. For example, an effective dose range may range from 0.01 to 100 milligrams per kilogram of body weight per day using administration by the intravenous route, such as in sterile normal saline.

The compound of this invention may be prepared by a novel method. The substitution of tryptophan in peptides may have been avoided in the past because Trp-peptides are acid sensitive. Bodanszky, et al., *J. Med. Chem.*, 23:1258-1261 (1980) and Sawyer, et al., *Endocrinology*, 106:81 (1980) made [Trp$^{-8}$] oxytocin by more difficult indirect methods, in order to avoid acid treatment of the Trp-peptide. The methods disclosed in U.S. Ser. Nos. 07/289,780 now abandoned and 07/433,664 now abandoned are hereby incorporated by reference.

Example I—Synthesis of [(S)Pmp$^1$,D-Trp$^2$,Pen$^6$,Arg$^8$] oxytocin

Synthesis of β-mercaptopropionic acid derivatives. Tetrahydrothiopyran-4-one, is reacted with triethylphosphonoacetate by the method of Wadsworth and Emmons (Wadsworth, W. S., Jr. Emmons, W. D. (1973) in *Organic Synthesis* (Baumgarten, H. ed.) Col. Vol. V, pp. 547-549, John Wiley & Sons, N.Y.), yielding ethyl 4-tetrahydrothiopyranylidene (TEP)acetate. Michael addition of 4-methylbenzyl mercaptan by the method of Yim and Huffman (Yim, N. C. F. & Huffman, W. F. (1983) *Int. J. Pept. Prot. Res.* 21, 568-570) and saponification yields tetrahydrothiopyranyl-4-(4-methyl-benzylthio)-4-acetic acid, or (S)PmP(S-Meb). See FIG. 1.

The abbreviations used comply with recommendations of the IUPAC-IUB Commission on Biochemical Nomenclature (J. Bio. Chem. 264, 688-673, (1989)). Where not indicated, amino acids are of the L-configuration. Other abbreviations used are: OT, oxytocin; Pmp, β,β-pentamethylene-β-mercaptopropionic acid; (S)Pmp, β,β-(3-thiapentamethylene)-β-mercaptopropionic acid; Boc, tert-butyloxycarbonyl; Meb, 4-methylbenzyl; Tos, p-toluenesulfonyl; ONp, 4-nitrophenyl ester; DCM, dichloromethane; TFA, trifluoroacetic acid; EtOH, ethanol; DIEA, diisopropylethylamine; DMF, dimethylformamide; DCC, dicyclohexylcarbodiimide; HOBt, 1-hydroxy Benzotriazole; MeOH, methanol; CHL, chloroform; Ac$_2$O, acetic anhydride; TEA, triethylamine; MeCN, acetonitrile; BuOH, n-butanol; AcOH, acetic acid; Pyr, pyridine; Et$_2$O, ethyl ether; HPLC, high performance liquid chromatography; TLC, thin layer chromatography; PITC, phenylisothiocyanate; PTC, phenylthiocarbamyl; UV, ultraviolet; OR, optical rotation.

Peptide synthesis

All protected peptides precursors of the antagonists were synthesized manually by the solid phase (SP) method (Merrifield, R. B. (1963) *J. Am. Chem. Soc.* 85, 2149-54). The Boc-amino acids (Stewart, J. M. & Young, J. D. (1984) in *Solid Phase Peptide Synthesis* pp. 1-176, Pierce Chemical Co., Rockford, IL) strategy of synthesis was followed. All position 1 analogs of Pmp had the thiol group protected with the 4-methylbenzyl group. Completion of coupling was monitored by means of the ninhydrin test (Kaiser, E., Colescot, R. L., Bossinger, C. D. & Cook, P. I. (1970) *Anal. Biochem.* 34, 595-598). Protected peptides were removed from the resins by ammonolysis (Manning, M., (1968) *J. Am. Chem. Soc.* 90, 1348-1349). Protected peptides were freed from blocking groups on side chain functionalities by reduction with Na/liquid ammonia (du Vigneaud, V., Ressler, C., Swan, J. M., Roberts, C. W., Katsoyannis, P. G. & Gordon, S. (1953) *J. Am. Chem. Soc.* 75, 4879-4880) or liq HF-anisole (Sakakibara, S. & Shimonishi, Y. (1965) *Bull. Chem. Soc. Jpn.* 38, 1412-1413) and the disulfhydryl peptides were cyclized in very dilute solution (Manning, M., Lammek, B. & Kolodziejczyk, A.M. (1981) *J. Med. Chem.* 24, 701-706) to the cyclic disulfide by oxidation with potassium ferricyanide (Hope, D. B., Murti, V. V. S. & du Vigneaud, V. (1962) *J. Biol. Chem.* 237, 1563-1566). The free peptides were freed from small by-products and salts by gel filtration (Porath, J. & Flodin, P. (1959) *Nature* (London) 183, 1657-1659) on SEPHADEX G-15(Manning, M., Wuu, T. C. & Baxter, J. W. M. (1968) *J. Chromatogr.* 38, 396-398) and by preparative high performance liquid chromatography (HPLC) (Flouret, G., Brieher, W., Mahan, K., and Wilson, L., Jr. (1991) *J. Med. Chem.* 34, 642-646). Peptide purity was monitored by TLC, HPLC, and amino acids analysis (Bidlingmeier, B. A., Cohen, S. A. & Tarvin, T. L. (1984) *J. Chromatogr.* 336, 93-104).

The peptide sequence of each analog was assembled manually by the SP method using a mechanical shaker and a special vessel. Where suitable some peptides were deprotected with liquid HF, using an all-TEFLON apparatus (Protein Research Foundation, Osaka, Japan). Boc-amino acids were supplied by Bachem, and synthetic or ionic resins were supplied by BioRad. all other reagents were supplied by Aldrich Chemical Co., Pierce, or Chemical Dynamics. The purity of peptides was checked by analytical HPLC with a Millipore apparatus previously described (Flouret, G., Brieher, W., Mahan, K., and Wilson, L., Jr. (1991) *J. Med. Chem.* 34, 642-646) and an analytical μBondapak C$_{18}$ column (30×0.39 cm). For preparative HPLC we used a Gilson auto-preparative HPLC System 71 as previously described (Flouret, G., Brieher, W., Mahan, K., and Wilson, L., Jr. (1991) *J. Med. Chem.* 34, 642-646) and a preparative column module 21.4 ×25 cm, with a guard module, 5 cm, both modules packed with DYNAMAX-60A, 8 μm, C$_{18}$ (Rainin). The solvents used for chromatography or synthesis were HPLC grade (Fisher Scientific). The solvent systems used both for analytical or preparative HPLC were: (a) 0.05% TFA; (b) 60% MeCN-40% solvent A. The purity of peptides was also monitored by thin-layer chromatography (TLC) on silica gel G pre-coated UNIPLATES (0.25 mm, Analtech). The solvent systems used (ratios given by volume ) were: (A) n-BuOH-AcOH-H$_2$O (4:1:1); (B) n-BuOH-AcOH:H$_2$O (4:1:5, upper phase); (C) n-BuOH-AcOH:-H$_2$O (5:1:1 ); (D) n-BuOH-AcOH:H$_2$O:Pyr (5:1:1:1 ). Peptides were visualized with Ehrlich reagent or chlorine-tolidine (Stewart, J. M. & Young, J. D. (1984) in *Solid Phase Peptide Synthesis pp.* 1-176; Pierce Chemical Co., Rockford, Ill.). For amino acid analysis analogs were hydrolyzed with 6N HCl for 24 hr. at 110° C. and the resulting amino acid components were derivatized with Phenylsiothiocyanate and analyzed by the Waters Associates Picotag method (using a Waters Picotag set up as previously described (Flouret, G., Brieher, W., Mahan, K., and Wilson, L., Jr. (1991) *J. Med. Chem* 34, 642–646). The optical rotations of peptides were measured with a Rudolph Polarimeter (precision±0.01°).

Solid-Phase Synthesis of Protected Peptides

Boc-amino acids were used for the synthesis, and for protection of side chain functionalities, Boc-Arg(Tos), Boc-Pen(Meb), and (S)Pmp(Meb). We used Boc-Gly-Resin (0.7 mmol of Boc-Gly/g) which was prepared on a 200–400 mesh cloromethylated resin (BioRad), 1% cross-linked with divinylbenzene, by esterification with the cesium salt of respective Boc-amino acid (Gisin, B. F. (1973) *Helv. Chim. Acta* 65, 1476–1482). The Boc-Gly-Resin (0.5–0.7 mmol/g) was taken manually through the required number of coupling cycles by the SP method of synthesis as previously modified (Flouret, G., Brieher, W., Mahan, K., and Wilson, L., Jr. (1991) *J. Med. Chem.* 34, 642–646). In each cycle the Boc group was removed with 30% trifluoroacetic acid in DCM and, after neutralization of the resin with 10% DIEA in DCM, coupling was performed with a three-fold excess of Boc-amino acid and DCC. Six molar excess of Boc-Asn-ONp or Boc-Gln-ONp in DMF was used at the appropriate steps, and the excess reagent was recovered by precipitation with water. Completion of the coupling step was monitored by means of the ninhydrin test which usually gave a negative response. If the test was positive, the coupling step was repeated, but if only faintly positive, the peptide was capped by acetylation with $Ac_2O$:DIEA:DCM (1:1:8). Unprotected Boc-D-Trp was introduced at position 2. The Boc-group was then removed with 30% TFA in DCM containing 1% mercaptoethanol and 10% anisole and (S)Pmp(S-Meb) was incorporated in 3 mole excess in DMF solution by activation with DCC and HOBt. The final assembled peptide was removed from the resin by ammonolysis with MeOH (25 ml) saturated with ammonia. After 3 days, the resin was removed by filtration, and extracted three times with hot DMF. The methanolic filtrate and the DMF extracts were pooled and evaporated to dryness. The residue was dissolved in DMF (2–3 ml) and the protected peptide amide was precipitated from the pooled DMF extracts by treatment with water or EtOH:$Et_2O$, yielding 400–600 mg of protected peptide. TLC analysis of protected peptides obtained after ammonolysis usually showed one major component with minor impurities, hence, they were used directly for deprotection and preparation of the free analogs.

Ethyl-4-tetrahydrothiopyranylidene acetate

This ester was prepared as described for the preparation of ethyl-4-tetrahydropyranylidene acetate (Wadsworth, W. S., Jr. Emmons, W. D. (1973) in *Organic Synthesis* (Baumgarten, H. ed.) Coll. Vol. V, pp. 547–549, John Wiley & Sons, New York) and vacuum distillation, oil (73% yield).

Tetradrothiopyranyl-4-(4-methyl-benzylthio)-4-acetic acid, or (S)Pmp(4-S-Meb)

This protected acid was prepared from the preceding ester, by the method of Yim and Huffman as described for Pmp (Int. J. Pept. Prot. Res. 21, 568–570, 1983), mp. 113-115[8] (50–70% yield).

[(S)$Pmp^1$,D-$Trp^2$,$Pen^6$,$Arg^6$]OT, or Antag III (S)Pmp(S-Meb)-D-Trp-Ile-Gln-Asn-Pen(Meb)-Pro-Arg(Tos)-Gly-$NH_2$ (600 mg), assembled by the SP method (starting with 0.5 mmole of amino acid-resin) as described above, was dissolved in liquid ammonia (200 ml) freshly distilled from sodium and treated under anhydrous conditions with a sodium stick until a pale blue color lasted for about 15–30 sec. After evaporation of ammonia in a vacuum, the solid residue was dissolved in 20 ml of 50% AcOH. This dissolved peptide was added to deaerated water (2 L) (this large volume can be sharply reduced by a modified procedure) the pH was adjusted to 7.0 by the addition of concentrated ammonium hydroxide and cyclization to the peptide disulfide was brought about by titration of the disulfhydryl peptide with 0.01N potassium ferricyanide until a permanent yellow color resulted and then adding 20% excess of potassium ferricyanide solution. After 20 min, the ferrocyanide and ferricyanide salts were removed by stirring for 10 min with AG1 X-2 ($Cl^-$) ion exchange resin (15 g.) and then by passing the suspension through a column containing additional ion exchange resin (15 g.), using additional 0.2N AcOH (100ml) for washings. The combined filtrate and washings were lyophilized. Analysis of the solid obtained containing the peptide was accomplished on an analytical μBondapak $C_{18}$ column (30×0.39 cm), monitoring at 220 nm, and eluting isocratically with 55% solvent B (solvent A, 0.05% TFA; solvent B 60% MeCN-40% of 0.05% TFA), at a rate of 1.8 ml/min. Under these conditions there was good resolution of impurities. The residue was dissolved in the smallest possible Volume of 50% acetic acid and was applied to a SEPHADEX G-15 column (115×2.7 cm) and eluted with the same solvent at a rate of about 50–60 ml/hr (6). The eluate was monitored in a UV spectrophotometer at 254 nm. The fractions corresponding to the major peak were monitored by analytical HPLC, with an analytical μBondapak $C_{18}$ column (30×0.39 cm), eluting with 57% solvent B, and detecting peptides at 220 nm. The pure fractions by HPLC criteria were pooled and lyophilized. The residue was dissolved in 0.2 N AcOH (20 ml) and was applied to a preparative DYNAMAX-60A, 8 μm, $C_{18}$ (Rainin) column, 21.4×25 cm, with a 5 cm guard module. A gradient was run from 0 to 45% B over 45 minutes, eluting at a rate of 5 ml/min, monitoring the eluent at 280 nm. Center portions of the main component eluted after approximately 3.5 hr. The purer fractions determined by analytical HPLC, were pooled and lyophilized, yielding Antag III (240 mg, 42% from initial resin). Analogue purity was established by thin layer chromatography (TLC) in four separate solvent systems, by analytical HPLC, and by amino acid analysis. The analogue gave the expected amino acid analysis ratios±10%. D-Tryptophan in peptides, was estimated by UV spectrophotometry at 280 nm (13). The lower value found for tryptophan, 0.96, suggests that the peptide lyophilisate may have TFA, and/or $H_2O$.

TABLE 1

| [alpha]$D^{27*}$-39° (1N, AcOH) | |
|---|---|
| TLC: (A) n-BuOH—AcOH—$H_2O$ (4:1:1) | Rf 0.27 |
| (B) n-BuOH—AcOH:$H_2O$ (4:1:5, upper phase) | 0.42 |
| (C) n-BuOH—AcOH:$H_2O$ (5:1:1) | 0.19 |
| (D) n-BuOH—AcOH:$H_2O$:Pyr (5:1:1:1) | 0.56 |

EXAMPLE II-Comparative testing of Compounds

For comparison with [(S)$Pmp^1$,D-$Trp^2$,$Pen^6$,$Arg^8$] oxytocin (antagonist D in Table 2), three related compounds were synthesized. One of these was the compound described by Manning, et al., *J. Med. Chem.*, 26:1607–1613 (1983). This compound can be called [Pmp$^1$,D-Phe$^2$,Phe$^3$,Ile$^4$,Arg$^8$] oxytocin. This compound is called antagonist A in Table 2. The other compound was [Pmp$^1$,D-Trp$^2$,Phe$^3$,Ile$^4$,Arg$^8$] oxytocin was disclosed in U.S. Pat. No. 07/239,780 now abandoned and is referred to as antagonist B in table 2. The third comparative compound [Pmp$^1$, D-Trp$^2$, Arg$^8$] oxytocin was disclosed in U.S. Ser. No. 07/433,664 now abandoned and is referred to as antagonist C in Table 2. The four compounds were comparatively studied in bioassays.

Oxytocic Bioassay

The protocol used for the oxytocin bioassay procedure is derived from procedures described in a paper by Sawyer, et al., *Endocrinology*, 106:81 (1980), which in turn was based on reports of Munsick, *Brit. J. Pharmacol.*, 3:328 (1960), and Holton, *Brit. J. Pharmacol.*, 3:328 (1948). The assay calculations for the pA$_2$ estimates are described by Schild, *Brit. J. Pharmacol.* (1947). The major difference in procedure from those previously reported was the integration of the area under the contraction instead of merely calculating the amplitude. Integration provides more consistent and reliable results, although the pA$_2$ estimates are about an order of magnitude lower than those reported using amplitude of the contraction as the endpoint.

Method: Animals

A 1.5 cm piece of uterus from a virgin rat (Holtzman) in natural estrus is used for the assay.

Buffer/Assay Bath

The buffer used is Munsick's. This buffer contains 0.5 mM Mg$^{++}$ which reduces the pA$_2$ estimates, but the results are reported to correlate better with the in vivo data (Sawyer, et al., 1980). The buffer is gassed continuously with 95% oxygen:5% carbon dioxide giving a pH of 7.4. The temperature of the assay bath is 37° C. A 10 ml assay bath is used that contains a water jacket for maintaining the temperature and inlet and outlet spikets for adding and removing buffer.

Polygraph/Transducer.

The piece of uterine tissue used for the assay is connected to a Statham Strain Gauge Force Transducer which in turn is attached to a Grass Polygraph Model 79 for monitoring the contractions.

Assay Protocol (a) The tissue is equilibrated in the assay bath for one hour with washing with new buffer every 15 minutes. One gram of tension is kept on the tissue at all times.

(b) The tissue is stimulated initially with oxytocin at 10 nM to "acclimate" the tissue and with 4 mM KCl to determine the maximum contractile response.

(c) A cumulative dose response curve is then determined with oxytocin and a concentration of oxytocin equivalent to approximately 80% of the maximum used for estimating the pA$_2$ of the antagonist.

(d) The tissue is exposed to oxytocin (Calbiochemical) for one minute and washed out. There is a three minute interval before addition of the next dose of the agonist or antagonist. When the antagonist is tested, it is given five minutes before the agonist. The agonist is given for one minute. All responses are integrated using a 7P10 Grass integrator. This is the major difference between our protocol and others in the literature who usually measure amplitude of the contractions as the response. A single concentration of oxytocin, equal to 80% of the maximum response, is used to test the antagonist. Three different concentrations of antagonists are used, two that will reduce the response greater than 50% (ideally this relation would be 25%, 50% and 75%). This is repeated three times for each dose of antagonist for a three point assay.

The anti-ADH activity is measured by the alteration in urine antagonist by ADH in the presence and absence of the antagonist to determine the specificity of the antagonist. The anti-ADH assay is described in Sawyer, et al., *Endocrinology*, 63:694 (1958).

Additional studies were performed to determine if the results of the rat bioassays reflected the binding affinity to the uterine OT receptors in the rat and human. The relative binding affinities of 5 different oxytocin antagonists were compared.

Oxytocin Receptor Assays

Method. Rats

Uterine tissue was removed on day 21 of pregnancy (delivery=Days 21$\frac{1}{2}$ to 22$\frac{1}{2}$) from Holtzman rats. The tissue was emptied of its contents, rinsed in ice cold buffer, cut into small pieces and frozen at −70° C. until homogenization.

Humans

Human myometrial tissue was collected from patients at the time of cesarian section after informed consent. The tissue was rinsed in cold buffer, cut into small pieces and frozen at −70° C. until homogenization.

Isolation of oxytocin receptors

Oxytocin receptors (OTrs) reside on the cell membrane and are present at high concentrations at the end of pregnancy in uterine tissue. Frozen tissue is homogenized in Tris buffer, the homogenate filtered, and the filtrate centrifuged at 1000 g for 15 minutes at 4° C. The supernatant is centrifuged at 40,000 g for 30 minutes and the pellet containing the cell membranes resuspended in 10% sucrose. Density gradient ultracentrifugation is then performed by placing the 10 % sucrose suspension on top of 35% sucrose and centrifuging for 30 minutes in a swing bucket rotor at 105,000 g. The membranes at the interface of the 10%/35% sucrose are removed and resuspended in Tris buffer containing EDTA for 30 minutes. This procedure removes divalent cation and results in dissociation of any endogenously bound OT to the receptor. This mixture is then centrifuged for 15 minutes at 100,000 g and the pellet containing the membrane OTrs resuspended in Tris, PMSF, Mg$^{++}$, buffer by sonication.

OT receptor assay

The binding assay consist of 0.1 ml of 20,000 cmp of tritium labeled OT (New England Nuclear, 37.1 Ci/n-mol), 0.1 ml of OT antagonist added at increasing concentration, 0.25 ml of buffer and 0.05 ml of membrane (70–150 ug protein). A nonspecific tube has 100× of cold OTA added to it. The incubation is for 30 minutes at 30° C. The membrane is pelleted by centrifugation in ultraclear mini tubes (5×41 mm) for 30 minutes at 105,000 g. The resulting pellet containing the bound $^3$H-OT is dissolved in 0.1N NaOH at 45° C. for 30 minutes and this mixture is then placed in liquid scintillation counting fluid and counted for dpms in a scintillation counter.

The data is analyzed by nonlinear curve fitting methods using McPherson's EBDA (*J Pharmacol Methods* 14:213–228, 1985) and Munson and Rodbard's LIGAND (*Anal Biochem* 107:220–239, 1980) program for saturation and competition analysis for determining Kds and Kis.

Results of the comparative bioassay and receptor studies are shown in Tables 2–4.

TABLE 2

| OTA* | Oxytocic Bioassay | | ADH Bioassay | | Ratio Anti-OT AntiADH |
|---|---|---|---|---|---|
| | pA$_2$ | Relative Anti-Oxytocic Activity | pA$_2$ | Relative Anti-ADH Activity | |
| A | 7.35 | 0.7 | 7.66 | 1.000 | 0.70 |
| B | 7.51 | 1.0 | 7.40 | 0.550 | 1.82 |
| C | 7.77 | 1.7 | 5.51 | 0.007 | 242.86 |
| D | 8.86 | 22.4 | <5.75 | 0.012 | >1866.7 |

*Compound A is [Pmp$^1$,D-Phe$^2$,Phe$^3$,Ile$^4$,Arg$^8$] oxytocin, as described by Manning, et al., *J. Med. Chem.*, 26:1607–1613 (1983).
Compound B is [$^{Pmp1}$,D-Trp$^2$,Phe$^3$,Ile$^4$,Arg$^8$] oxytocin = ANTAG I
Compound C is [Pmp$^1$,D-Trp$^2$,Arg$^8$] oxytocin = ANTAG II.
Compound D is [(S)Pmp$^1$,D-Trp$^2$,Pen$^6$,Arg$^8$] oxytocin = ANTAG III.

In Table 2, Compound D, comprising the novel compound of this invention, demonstrated a higher anti-oxytocic activity than of the other three compounds. Further, it had a much lower anti-ADH activity. The ratio of anti-OT/anti-ADH for Compound D is greater than 1, 866.70, while this ratio for Compound A was 0.7, Compound B 1.8 and Compound C 242.9. These data therefore indicate that Compound D can be expected to produce less anti-ADH side effects when administered at an effective oxytocin antagonist dose than either Compounds A, B or C.

Table 3 illustrates the comparison of the binding affinities (Kas) estimated from the rat uterine receptor assay (Kas) versus the bioassay. Correlation of the Log$_{10}$ Ka with Log$_{10}$ED$_{10}$ was highly significant (r=0.92; p<0.01). Comparison of the relative activity of ANTAG III (compound D) to ANTAG I (compound B) by the rat uterine receptor assay and bioassay is shown in Table 5. By both assays ANTAG III is approximately 20× more potent than ANTAG I.

Table 4 shows the binding affinity of the different OTAs to the human uterine OTr compared to the rat bioassay. Correlation of the Log$_{10}$ Ka to the Log$_{10}$ ED$_{50}$ was highly significant (r=0.95; p<0.01). Comparison of the relative binding activity of ANTAG III versus ANTAG I to the human OTr (hOTr) is shown in Table 5. By this estimate ANTAG III (compound D) is about 80× more potent than ANTAG I. Therefore, it appears that the rat assays might be under estimating the relative potency of ANTAG III in the human. This possibility is further supported by the in vivo studies performed in the pregnant baboon described below.

Example III testing of Compounds in Pregnant Baboons

The purpose of this study was to ascertain the relative in vivo activity of four oxytocin antagonist using the tethered pregnant baboon model and compare these results to previous activity estimates using rat assays and human OTr assays. The baboon is an excellent animal model because of its physiologic and anatomic similarity to humans (see articles by our laboratory: *Am J Obstet Gynecol*. 163:1815–1882, 1990; *Am J Obstet Gynecol* 165:456–560, 1991; *Am J Obstet Gynecol* 165:1487–1498, 1991; articles by other laboratories: *Endocrine Reviews* 11:124–150, 1990; 11:151–176, 1990). Pregnant tethered baboons were studied between 130 to 145 days of pregnancy Delivery=day 184). The oxytocin antagonists were administered as a single bolus injection of 1 mg intra-arterially followed 1 minute later by the infusion of oxytocin. Oxytocin was infused continuously beginning at 10 mU and doubling the dose every 20 minutes up to 400 mU/minute or until the contractile force (CF=(freq×mean amplitude)/10 minutes] response was significant (i.e. CF>50). If there was no significant response the oxytocin challenge test was repeated 24 hours later. The antagonists-response interval (ARI) was determined by multiplying the time to the first significant response in minutes by the contraction to pulse ratio (CF/OT concentration). Results: The results are shown in Table 5. The ARI was highly correlated with the rat and human OTr estimates of binding affinity (Ka) (r-0.98; p<0.01) with 4/5 oxytocin antagonists. One oxytocin antagonist (antagonist F in Table 5) showed no inhibitory activity at the dose tested although it had moderately good binding affinity in the rat and human OTr assays and rat bioassay. This oxytocin antagonist was not produced in our laboratory and is not an oxytocin analog. One mg of the best oxytocin antagonist tested (Compound D, the novel compound of this invention) blocked the response to oxytocin antagonist for greater than 24 hours. Comparison of the relative activities of the different OTAs to compound B (ANTAG I) suggests that compound D, [(S)PMP$^1$,D-Trp$^2$,Pen$^6$,Arg$^8$] oxytocin (i.e. ANTAG III) is about 130 times more potent than compound B. In summary, the relative activity ratios (see Table 5) of ANTAG III (D) to ANTAG I (B) by rat bioassay, rat receptor assay, human receptor assay and in vivo baboon bioassay were 22, 20, 82 and 133, respectively. These data indicate that the rat assays might be underestimating the potency of ANTAG III in primates.

TABLE 3

COMPARISON OF RELATIVE UTERINE RECEPTOR BINDING (Ka) AND BIOASSAY INHIBITORY ACTIVITY (ED50) FOR OXYTOCIN ANTAGONISTS

| Oxytocin Antagonist | RECEPTOR ASSAY Ka(10$^{+8}$M$^{-1}$) | OXYTOCIC BIOASSAY ED50 (nM) |
|---|---|---|
| A | 0.39 | 44.76 |
| B | 1.16 | 30.90 |
| C | 2.03 | 16.98 |
| C2 | 11.50 | 1.91 |
| D | 24.40 | 1.38 |
| E | 0.51 | 102.33 |
| F | 5.89 | 19.93 |

RECEPTOR ASSAY - PREGNANT RAT UTERUS (P-21)
BIOASSAY - ESTROUS RAT UTERUS
A - DESCRIBED BY MANNING ET AL. J. MED. CHEM. 26:1607, 1983
B - [Pmp$^1$, D-Trp$^2$, Phe$^3$, ILe$^4$, Arg$^8$] OXYTOCIN = ANTAG I
C - [Pmp$^1$, D-Trp$^2$, Arg$^8$] oxytocin = ANTAG II
C2 - [Pmp$^1$, D-Trp$^2$, Pen$^6$, Arg$^8$] oxytocin = ANTAG II-2
D - [(S)PMP$^1$, D-Trp$^2$, Pen$^6$, Arg$^8$] oxytocin = ANTAG III
E - [Mpa$^1$,D-Tyr(Et)$^2$,Thr$^4$, Orn$^8$] oxytocin (ie.ATOSIBAN)
F - L-366,948 FROM MERCK PHARMACEUTICAL

TABLE 4

COMPARISON OF UTERINE RECEPTOR BINDING (Ka) IN HUMAN MYOMETRIAL TISSUE TO RAT UTERINE BIOASSAY INHIBITORY ACTIVITY (ED50) FOR OXYTOCIN ANTAGONISTS

TABLE 4-continued

| OTA | RECEPTOR ASSAY $K_a(10^{+8}M^{-1})$ | BIOASSAY $ED_{50}(nM)$ |
| --- | --- | --- |
| B | 0.51 | 30.9 |
| C | 1.82 | 17.0 |
| D | 41.7 | 1.38 |
| E | 0.53 | 102.3 |
| F | 2.49 | 20.0 |

RECEPTOR ASSAY - MYOMETRIAL TISSUE TAKEN FROM WOMEN AT TERM BY C-SECTION

BIOASSAY - ESTROUS RAT UTERUS

COMPOUNDS B-F ARE DESCRIBED IN TABLE 3

TABLE 5

COMPARISON OF THE RATIOS OF BIOLOGIC ACTIVITY (ARI) OF 5 OXYTOCIN ANTAGONISTS (OTAs) IN THE PREGNANT BABOON TO THE RATIOS OF OXYTOCIN RECEPTOR (OTr) BINDING AFFINITY AND BIOASSAY ACTIVITY IN THE RAT AND HUMAN

| OTA | ARI | ARI (OTA/ ANTI) | rOTr (OTA/ ANTI) | hOTR (OTA/ANTI) | BIOASSAY (ANTI/OTA) |
| --- | --- | --- | --- | --- | --- |
| B | 59 | 1 | 1.0 | 1.0 | 1.0 |
| C | 547 | 9 | 1.8 | 3.6 | 1.8 |
| D | 7856 | 133 | 20.0 | 81.8 | 22.1 |
| E | — | — | 0.4 | 1.0 | 0.3 |
| F | 0 | 0 | 5.1 | 4.9 | 1.5 |

ARI - ANTAGONISTS-RESPONSE INTERVAL IN THE PREGNANT BABOON (SEE TEXT FOR EXPLANATION OF CALCULATION)
rOTr - RAT OXYTOCIN RECEPTOR
hOTr - HUMAN OXYTOCIN RECEPTOR
BIOASSAY - RAT OXYTOCIC BIOASSAY
ANTI-ANTAG I
COMPOUNDS B-F ARE DESCRIBED IN TABLE 3.

Although the invention has been described primarily in connection with special and preferred embodiments, it will be understood that it is capable of modification without departing from the scope of the invention. The following claims are intended to cover all variations, uses, or adaptations of the invention, following in general, the principles thereof and including such departures from the present disclosure as come within, known or customary practice in the field to which the invention pertains, or as are obvious to persons skilled in the field.

We claim:

1. An oxytocin antagonist represented by the formula

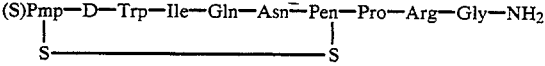

wherein (S)Pmp IS $\beta,\beta$-(3-thiapentamethylene)-$\beta$-mercaptopropionic acid, D-Trp is the D form of tryptophan, and Ile, Gln, Asn, Pen (Pen=penicillamine), Pro, and Arg are the L forms of isoleucine, glutamine, asparagine, proline and arginine, respectively.

* * * * *